United States Patent [19]

Kaplan et al.

[11] Patent Number: 4,668,629
[45] Date of Patent: May 26, 1987

[54] HUMAN HYBRIDOMAS, PRECURSORS AND PRODUCTS

[75] Inventors: Henry S. Kaplan, Stanford; Lennart Olsson, Palo Alto, both of Calif.

[73] Assignee: The Board of Trustees of Leland Stanford Jr. University, Stanford, Calif.

[21] Appl. No.: 599,201

[22] Filed: Apr. 9, 1984

Related U.S. Application Data

[63] Continuation of Ser. No. 170,255, Jul. 18, 1980, abandoned.

[51] Int. Cl.⁴ .................. C12N 5/00; C12N 15/00
[52] U.S. Cl. .................. 435/172.2; 435/240; 935/93; 935/99; 935/107; 424/85
[58] Field of Search .................. 436/513, 548; 260/112 R; 935/89, 92, 90, 93, 95, 106, 110, 111, 99, 107; 435/172.2, 240, 948, 68; 424/85

[56] References Cited

U.S. PATENT DOCUMENTS 4,172,124 10/1979 Koprowski .................. 424/85
4,196,265 4/1980 Koprowski et al. .................. 435/2

OTHER PUBLICATIONS

Kohler et al, Nature 256, (Aug. 7, 1975), 495–497.
Bouman, Chem. Abs., vol. 85, 1976, Ab. No. 85:3692t.
Freedman, Immunochem., vol. 13, 1976, pp. 193–202.
Nilsson, Clin Exp Immunol., vol. 7, 1970, pp. 477–489.
Koprowski, Lymph. Hybridomas, Curr. Topics in Microbiol. Immuno, vol. 81, 1978, Springer Verlag, N.Y., pp. 8–19.
Bloom, Chem. Abs., vol. 81, 1974, Ab. No. 134359e.
Milstein, Sci. American, vol. 243, Oct. 1980, pp. 66–74.
Gronowicz, J. Immunol, vol. 125, Sep. 1980, pp. 976–980.
Brown, J. Immunol., vol. 125, Sep. 1980, pp. 1037–1043.
Kohzoh, Chem. Abs., vol. 94, 27 Apr. 1981, Ab. No. 94:137651y.
Larizza, Chem. Abs., vol. 93, 27 Oct. 1980, Ab. No. 93:165698s.
Kenneth (Ed.), Monoclonal Antibodies–Hybridomas: A New Dimension in Biol. Anal., Plenum Press, N.Y., Jul. 1980, pp. 137–153.
Nowinsky, Sci., vol. 210, 31 Oct. 1980, pp. 537–539.
Croce, Nature, vol. 288, 4 Dec. 1980, pp. 488–489.
Trucco, Nature, vol. 273, 22 Jun. 1978, pp. 666–668.
Croce, Nat. Acad. Sci., Proc. USA, vol. 76, Jul. 1979, pp. 3416–3419.
Dolby, Nat. Acad. Sci., Proc., USA, vol. 77, Oct. 1980, pp. 6027–6031.
Olsson, Nat. Acad. Sci., Proc. USA, vol. 77, Sep. 1980, pp. 5429–5431.
Levy, Nat. Acad. Sci., Proc. USA, vol. 75, May 1978, pp. 2411–2415.
Pellegrino, Chem. Abs., vol. 93, No. 7, 18 Aug. 1980, Ab. No. 93:68428w.
Kohler, Nature, vol. 356, 1975, pp. 495–497.
Kohler, Euro. J. Immunol., vol. 6, 1976, pp. 511–519.
Levy, PNAS, USA, vol. 75, 1978, pp. 4211–4215.
Steinitz, Nature, vol. 269, 1977, pp. 420–422.
Melchers, Lymph Hybridomas, Current Topics in Microbiol. & Immuno., vol. 81, 1978, Springer Verlag, N.Y., pp. IX–XXIII; Table of Contents, 3 pages.
Margulies, Dissertation, Xerox Uni Microfilm, Ann Arbor, Mich., Jun. 1977, No. 7800059, pp. 22, 23, 30–33.

Primary Examiner—Esther M. Kepplinger
Assistant Examiner—David A. Saunders
Attorney, Agent, or Firm—Bertram I. Rowland

[57] ABSTRACT

Human monoclonal antibody compositions, human-human monoclonal hybridoma cells, human myeloma cells, human antibody genes and their uses. Human myeloma cells are developed for fusing with immunized lymphoid cells to provide stable human-human hybridoma strains producing complete monoclonal antibodies for a predefined antigen. From a myeloma cell line, rapidly growing 8-azaguanine resistant HAT sensitive cells are selected. The selected myeloma cells are crossed with immunized lymphoid cells and the resulting cell mixture grown under controlled selective conditions. After expansion of the desired hybridoma cells, the monoclonal antibodies may be harvested. The hybridomas serve as a source for messenger RNA for light and heavy chains which may be used for production of light and heavy chain immunoglobulin proteins through hybrid DNA techniques.

5 Claims, No Drawings

HUMAN HYBRIDOMAS, PRECURSORS AND PRODUCTS

This work was supported in part by grant CA 05838 from the National Cancer Institute, National Institute of Health.

U-266-AR$_1$ cell line has been deposited at Cell Distribution Center. The Salk Institute on July 17, 1980. The SKO-007 line was deposited at the ATCC on Sept. 11, 1980 and given the designation CRL-8033.

CROSS-REFERENCE TO RELATED APPLICATIONS

This is a continuation of application Ser. No. 170,255, filed July 18, 1980, now abandoned, which disclosure is incorporated herein by reference.

BACKGROUND OF THE INVENTION

1. Field of the Invention

The mammalian capacity for producing immunoglobulins has found application in medicine and industry. The ability of immunoglobulins to distinguish specifically between chemical compounds of slightly differing structure has found broad application in the detection and measurement of a wide variety of compounds. In therapeutic applications, immunoglobulins can be administered to provide passive immunity against diseases. Major stumbling blocks in the wide application of immunoglobulin therapy were the heterogeneity of antisera and the limited availability of human antisera for a specific antigen.

The seminal discovery by Kohler and Milstein of mouse "hybridomas" capable of secreting specific monoclonal antibodies against predefined antigens ushered in a new era in experimental immunology. Many of the problems associated with antisera are circumvented; the clonal selection and immortality of such hybridoma cell lines assure the monoclonality and permanent availability of their antibody products. At the clinical level, the use of such antibodies is clearly limited by the fact that they are foreign proteins and would act as antigens to humans.

Human cells have only been difficulty cultured in vitro. Efforts to achieve a human hybridoma which is a cross between a lymphoid cell and a myeloma cell have heretofore been unsuccessful. The problems of maintaining a stable culture of human cells have inhibited the ready production of human-human hybridomas.

2. Description of the Prior Art

The production of mouse hybridomas is described by Kohler, G. and Milstein, K. (1975) Nature 356: 495–7; (1976) Euro. J. Immunol 6: 511–519. Chimeric hybridomas generated by fusing mouse myeloma cells with human immunoglobulin-producing cells is described by Levy, R. and Dilley, I. (1978) PNAS USA 75: 2111–2415. Permanent cultures of specific antibody-producing human B-lymphocytes obtained by transformation with Epstein-Barr virus is described by Steinitz, M. (1977) Nature 269: 420–422.

DESCRIPTION OF THE SPECIFIC EMBODIMENTS

In accordance with the subject invention, a novel human myeloma strain is provided, which is employed for fusion with lumphoid cells to produce hybridomas capable of producing complete monoclonal antibodies having a unique specificity and homogeneous composition. The invention therefore involves the development of the myeloma strain; the preparation of lymphoid cells producing antibodies to a specific antigen; the fusion of the immunized lymphoid cells and myeloma cells to produce hybridoma cells; the selective culturing of the hybridoma cells; and the production of monoclonal antibodies. The antibodies may be produced to a wide variety of haptens and antigens and may find use in immunoassays, passive immunization, treatment against infection, diagnosis and treatment of cancer, and the like. In addition to the production of IgG, human-human hybridomas offer opportunities for the production of complete human monoclonal IgA, IgM, and IgE.

The human-human hybridomas can also serve as a useful source of mRNA for the heavy and light chains of antibodies for specific antigens. By known molecular biology techniques, the mRNAs may be used for the generation of genes which when inserted into the appropriate vector can serve as a source of the proteins. Upon assembling of the light and heavy chains, antibodies are produced.

HUMAN MYELOMA CELL LINE

The human myeloma cell line is chosen to provide a stable cell line which is HAT medium sensitive and unable to metabolize hypoxanthine. The particular cell line chosen was U-266 which was originally described by Nilsson, K. et al., (1970) Clin. Exp. Immunol 7: 477–489.

HAT sensitivity is achieved by culturing cells in a medium containing a purine analog such as 8-azaguanine. Cells remaining viable under these conditions are mutants lacking an alternative biosynthetic pathway for the production of purines.

Specifically, the cells are first cultured at a high 8-azaguanine concentration, then at a low 8-azaguanine concentration, followed by cultivation at intermediate concentration levels. In each instance, incubation times are about one week, with the viable cells being isolated prior to the next incubation. The 8-azaguanine concentration varies in the range of about 3 to 25 $\mu$g/ml, usually in the range of about 5 to 20 $\mu$g/ml. At each stage the number of cells being incubated should be sufficient to ensure the isolation of viable cells at the end of the incubation. There should be at least $1 \times 10^3$, preferably $5 \times 10^3$ cells per microliter plate well.

The number of successive incubations with nutrient media containing 8-azaguanine will be at least two and not more than about eight.

Selection is further made of the fastest growing 8-azaguanine resistant HAT sensitive clones and it is these clones that are expanded. Rapidly growing clones normally double in about 24 to 36 hours.

Except for the 8-azaguanine and HAT, the nutrient media employed are conventional. Prior to fusion the selected cells are expanded in non-selective nutrient medium to enhance the number of cells.

HUMAN LYMPHOID CELLS

The human lymphoid cells are cells immunized against a hapten or antigen. Various sources of lymphoid cells may be employed. One source is spleen specimens, which specimens are devoid of malignancies. The host should be immunized at least once, and at least about two weeks prior to the splenectomy. After freeing a single cell suspension of the spleen tissue of red blood cells and granulocytes, the viable mononuclear cells are suspended in an appropriate nutrient medium, and non-adherent cells separated from adherent cells. The lymphoid cell culture may then be fused with the myeloma cell line.

Instead of In vivo immunization, spleen cells can be isolated and immunized in vitro. A single cell suspension of spleen cells is prepared, viable cells are isolated and seeded in nutrient medium with the appropriate antigen at an appropriate concentration. After sufficient time for immunization, viable cells are isolated and used for fusion.

An alternative to spleen lymphoid cells are lymphocytes isolated from peripheral blood, which are then combined in an appropriate nutrient medium containing macrophages and a sufficient amount of an antigen to prime the lymphocytes. After a sufficient time for priming, generally from about two to four days, the viable cells may be separated from the dead cells and employed for fusion. The lymphocyte cells can be isolated by Ficoll-Hypaque gradient centrifugation and viable cells grown in nutrient medium, containing about 15% FCS, about 40 µg/ml antigen, and about $10^5$ macrophages/ml and the cells incubated for three days to prime the cells and produce blast cells. The viable cells may then be used for fusion.

FUSION

The fusion is carried out by combining the myeloma cells and lymphoid cells in an appropriate non-ionic detergent containing medium, normally polyethylene glycol of from about 1000 to 6000 daltons. The period for the fusion is generally under about 3 min. and the resulting cells are rapidly washed free of the non-ionic detergent. While ratios other than 1:1 of the two cell lines may be employed, the best results have been obtained with a 1:1 ratio. Therefore, for enhanced probability of success in the fusion and isolation of desired hybridoma cells, an approximately 1:1 ratio of cells should be employed. The individual cell concentration will generally be from about $10^6$ to $10^8$, preferably about $1-2\times10^7$ cells/ml. The cells are then seeded at relatively high concentrations in microplates in nutrient media, there being at least about $10^4$–$10^6$ cells per well, preferably about $1-2\times10^5$ cells per well. After a sufficient time for expansion, generally 1–4 days, usually about 2 days, the cells are then selected by incubation in HAT medium. While normally HAT resistant hybrids grow out within about one to two weeks, it is desirable that the culture be expanded in HAT medium for from about three to four weeks.

The HAT medium which is employed is described in Littlefield, Science 145, 709 (1964) and contains a combination of hypoxanthine, aminopterin or methotrexate, and thymidine.

After the initial incubation with the HAT medium, the supernatant fluid of each culture microwell is tested for immunoglobulin production. Conveniently, Staph. protein A-binding can be employed for detection of IgG and IgA ($\alpha_2$). If detection of other immunoglobulins is of interest, radio-labeled heterologous antisera to specific types of heavy chains can be used for the detection of each of the other types of immunoglobulins. Conveniently, any immunoassay may be used which can distinguish the various immunoglobulins, such as radioimmunoassays.

Once positive wells are detected, the cells in the positive wells may be cloned under limiting dilution conditions. The resulting clones are then expanded and the monoclonal antibodies are then harvested in accordance with known procedures. The monoclonal antibodies may be freed of other proteins in accordance with known techniques, such as electrophoresis, chromatography, or the like.

MONOCLONAL ANTIBODIES

By appropriate immunization, the monoclonal human antibodies may be prepared against any hapten or antigen. By antibodies is intended to include not only IgG, but also IgM, IgE and IgA. Particularly, antibodies may be produced against drugs, both naturally occurring and synthetic, such as opioids, amphetamines, barbiturates, steroids, catecholamines, dilantin, theophylline, histamine, PCP, cannabinoids, or the like.

Antigens of interest include histocompatability antigens, pathogen surface antigens, viral antigens, toxins, allergens, and the like.

For a more complete list of ligands of interest, see U.S. Pat. No. 4,193,983 particularly columns 7-11 inclusive, which disclosure is incorporated herein by reference.

As indicated previously, the subject invention provides for production of the various immunoglobulins IgG, IgM, IgA and IgE. As compared to previous immunoglobulin compositions, the subject compositions are homogeneous in composition. That is, greater than 90 weight %, usually greater than about 95 weight %, more usually greater than about 99 weight % will have the same composition.

By referring to the same composition it is intended that the chemical composition of the chains be the same; the chains be of substantially the same chain length, normally the same chain length; and the folding of the molecules be substantially the same to define the same specificity. In effect, the primary, secondary and tertiary structures of the immunoglobulin molecules in the composition are substantially the same.

By having a uniform composition of immunoglobulins many advantages ensue. First, one is ensured of freedom from immunoglobulins specific for other than the predefined antigen. The presence of undesired immunoglobulins is disadvantageous for analytical work as well as for therapeutic purposes. Secondly, one is assured of a single binding site, as compared to antibody compositions obtained from myeloma patients. Third, one can obtain an exact titer for a specific determinant site, rather than averaging over the entire composition. With analytes, better control of cross-reactivities can be achieved with a homogeneous composition.

The subject monoclonal human antibodies find use in conventional applications for antibodies, such as immunoassays, cell sorting, electrophoretic analysis, histology, cytology and the like. Besides the conventional uses, the subject monoclonal human antibodies have additional uses since they are not xenogeneic (foreign) proteins for other humans.

Because the human monoclonal antibodies will be accepted by the human immune system, the monoclonal human antibodies can be used for induction of passive immunity. Among immune sera which are presently available are antisera for tetanus, hepatitis, vaccinia, mumps, rabies, pertussis, botulism, gas gangrene, varicella, as well as other diseases.

The antisera are normally administered parenterally or by ingestion in dosages varying from 100 to 20,000 units, or in amounts based on immune serum of 0.005 to 1 ml/kg of the host. (Medical Pharmacology 6th ed.

Edited by Meyers, Jaivetz and Goldfien, Lange Medical Publications, 1978, pages 612-615.) Particular dosages will vary depending upon the manner of administration. Various carriers or media can be used, such as physiological saline, capsules, plasma, or the like. Other additives may also be included, such as stabilizers, drugs, proteins, and the like.

The human monoclonal antibodies can also be used for site directed therapy. By preparing antibodies recognizing determinant sites of an organ, abnormal cell e.g. tumor, or infectious cell, the antibody can serve to direct a drug or other therapeutic means to such site and maintain such drug or therapeutic means at such site. For example, the antibodies can be attached to slow release particles containing a particular drug for treatment of an infection. The antibodies would bind to the infected site, maintaining a high localized concentration of the drug in the infected area.

Other uses include diagnosis, where the antibodies would be radioactively labeled, providing for localization of the radioactive label at a particular site, permitting radiography at a particular organ or other internal site.

The hybridomas can also serve as a concentrated source of messenger RNA or as a source of the genes for the light and heavy chains of IgG.

The desired messenger RNAs mahy be obtained as follows. The hybridoma cells are swolen on ice, ruptured, the nuclei removed by centrifugation, the supernatant isolated and centrifuged to produce a pellet containing the membrane-bound polysomes. The pellet is resuspended in appropriate medium, deproteinized by conventional means and the RNA precipitated by adding buffer and ethanol.

The poly A-rich mRNA can be concentrated with an oligo dT-cellulose or poly dU-Sepharose chromatographic column. The mRNA mixture is then resolved employing density gradient centrifugation and/or gel electrophoresis and the fractions collected.

The mRNA fractions may then be assayed for in a number of ways. The mRNA from the parent myeloma cell may be treated in the same way and common bands between the mRNA from the hybridomas and the myeloma cells discarded. mRNA molecules of the appropriate molecular weights for the light and heavy chains can be employed under the same conditions of density gradient centrifugation to further narrow the number of bands.

For further elimination of mRNA molecules other than those expressing the desired light and heavy chains, probes can be prepared of RNA or ssDNA. The probes are synthesized from nucleotides corresponding to the codon sequence coding for a portion of the polypeptide light and heavy chains respectively. The probe will usually have at least 20 bases, preferably at least about 30 bases. A $^{32}P$ marker is employed for autoradiographic visualization.

The probe is hybridized with the electrophoretic fractions under conditions where only mRNA substantially homologous with the probe will hybridize. (See, Southern, J. Mol. Biol. 98, 503 (1975)). Where the probe is based on the variable portions of the light and heavy chains, only the desired mRNAs will be isolated, or highly concentrated fractions thereof.

It is not necessary, however, to isolate the mRNAs expressing the desired light and heavy chains. Purification can be achieved subsequently by isolation of transformants producing the desired light and heavy chains, employing antisera to the chains for detecting the desired clones.

After isolating the mRNAs substantially pure or as a mixture, cDNA may be prepared by employing reverse transcriptase in accordance with conventional techniques (Buell, et al. J. Biol. Chem. 253: 2471 (1978)). The dsDNA is generated using DNA polymerase and S1 nuclease (Wickens, et al., ibid 253: 2483 (1978)). Sequencing of the 5'-ends will determine the sites of initiation of the light and heavy chains. The DNA sequence preceding the f-met codon may be removed employing an exonuclease and replaced with a short sequence providing cohesive ends, a host ribosomal start site or other appropriate coding.

The dsDNA for the light and heavy chains may be joined to any conventional vector by conventional means. Vectors will normally have a marker, conveniently antibiotic resistance, for selection of transformants. Illustrative vectors include pSC101, λplac, pBR322, YIp5, and the like which may be used for transformation of bacteria and yeast. The dsDNA may be joined to the vector by means of blunt end ligation, for example, with T-4 ligase; or the termini modified, by ligation of a short dsDNA having a staggered end and a blunt end to provide for cohesive ends; or by adding on complementary sequences employing deoxynucleotidyl transferase. As indicated previously, modification of the termini can be used for introducing particular signals, providing for binding to the vector, as well as providing restriction sites. The dsDNA is joined to the replicon to provide a ribosomal start site near the f-met codon. Various techniques are available for either introducing a ribosomal start site on the dsDNA adjacent to f-met codon or joining the gene adjacent the ribosomal start site of the vector.

The vector and dsDNA are joined under hybridizing and ligating conditions to produce circular DNA or plasmids and host cells transformed under transforming conditions e.g. calcium shock. The cells are then grown under selective conditions to kill any untransformed host cells. The remaining viable cells are streaked on selective media and individual clones grown and tested for production of the desired light and heavy chains. The light and heavy chains are isolated from the clones, by rupturing the cells and then employing conventional separation techniques, such as density gradient centrifugation, electrophoresis, chromatography, and the like. The purified light and heavy chains are then combined under mildly oxidizing conditions to provide for folding of the chains together and disulfide formation.

As an alternative to employing the mRNAs, the DNA may be synthesized based on the mRNA sequence. See European Patent Application 0 001 929. Oligodeoxyribonucleotides can be prepared and joined together to provide ssDNA. The coding strand of ssDNA can be synthesized with appropriate host signals, e.g. ribosomal start and stop, promoter and operator signals. Also, appropriate restriction sites are provided at the termini for joining to the vector and retrieving the genes after cloning. Once the gene has been synthesized, it may be inserted into a replicon as described above.

The following examples are offered by way of illustration and not by way of limitation.

EXPERIMENTAL

In order to demonstrate the subject invention, the following preparation was carried out. A HAT medium sensitive mutant cell line was selected from the U-266 human myeloma cell line originally described by Nilsson et al. supra. U-266 cells were incubated for one week in RPMI-1640 medium containing 15% FCS and 20 μg/ml 8-azaguanine; dead cells were then removed by Ficoll-Hypaque gradient centrifugation and viable cells were incubated in RPMI-1640 plus 15% FCS plus 5 μg/ml 8-azaguanine for three days followed by isolation of viable cells using a Ficoll-Hypaque gradient. The viable cells were then seeded in one well $0.5 \times 10^3$ cells). The cells are then grown at gradually increasing concentrations of 8-azaguanine going from 5 to 20 μg/ml at 5 μg/ml increments for 1 week at each concentration. The viable cells are then maintained in RPMI-1640 plus 15% FCS plus 20 μg/ml 8azaguanine. Cultures of the fastest growing 8-azaguanine resistant clone were expanded, after verifying that they were HAT sensitive. This mutant cell line, U-266-AR$_1$ was maintained in RPMI-1640 plus 15% FCS plus 5 μg/ml 8-azaguanine. The cells are seeded at a concentration of $10^5$/ml 3–5 days before fusion. On the day of fusion, the cell concentration is about $0.8–1.0 \times 10^6$ cell/ml. The viability is above 90%.

Fresh spleen specimens were obtained from untreated patients with Hodgkin's disease undergoing staging laparotomy with splenectomy. The spleens were devoid of involvement by Hodgkins disease. At least two weeks prior to surgery, such patients were sensitized and later challenged with 2-dinitrochlorobenzene.

A single cell suspension prepared from the spleen tissue was freed of red blood cells and granulocytes by Ficoll-Hypaque gradient centrifugaion and the viable mononuclear cells suspended in RPMI-1640 medium. Adherent cells were removed by incubation of the mononuclear cells in plastic dishes three times for 20 mins. each at 37° C. and removal of the non-adherent cells after each incubation. The lymphocyte-enriched monoculear cell suspensions thus obtained were then fused with U-266-AR$_1$ human myeloma cell line.

Fusion was achieved by mixing $2 \times 10^7$ myeloma cells and $2 \times 10^7$ lymphoid cells, washing twice in RPMI-1640 and then fusing in 2.0 ml 38% w/v polyethylene glycol ($\sim$1400 mw) at 37° C. After the last wash, the supernatant is removed as quickly as possible and the polyethylene glycol added dropwise over a minute at 37° C. The cell pellet is carefully stirred for 1 min. in polyethylene glycol, then gently resuspended with a 1 ml pipette. The cells are centrifuged at 400 rpm for 4 mins. and 800 rpm for 4 mins. The polyethylene glycol supernatant is discarded, the pellet resuspended in warm (37° C.) serum-free RPMI-1640 and washed twice with warm (37° C.) RPMI-1640 medium, and then suspended at a concentration of $10^6$ cells/ml in RPMI-1640 plus 15% FCS. The cells are seeded in 0.2 ml aliquots in microtiter plates with flatbottom wells in RPMI-1640 plus 20% FCS and then incubated in the same medium for 48 hrs. After 48 hrs., the medium is changed to HAT medium and the cells incubated in HAT medium for eight days. The HAT medium is $10^{-4}$M hypoxanthine; $6.3 \times 10^{-8}$M methotrexate; $1.5 \times 10^{-6}$M thymidine; 40 i.u./ml insulin and 13.2 mg/100 ml oxaloacetic.

The supernatant fluid of each culture microwell is then tested for immunoglobulin production by employing a solid-phase radioimmunoassay using $^{125}$I labeled Staph. protein A as the detector. This test is only diagnostic of IgG ($\gamma_1$, $\gamma_2$, $\gamma_4$) and IgA($\alpha_2$). Therefore, production of other immunoglobulins such as IgM and IgE would go undetected. By employing appropriate antibodies, the other types of immunoglobulins could also be detected.

Cultures containing immunoglobulin producers were expanded for two days in RPMI-1640 plus 20% FCS plus 40 i.u./ml insulin. After two days, the culture was grown in HAT medium for another 1–2 weeks. Wells that showed immunoglobulin production were then tested for production of antibodies binding specifically to dinitrophenyl-BSA. Several anti-dinitrophenyl antibody-producing cultures were detected. Cells from such wells were cloned by limiting dilution procedure and cultures of the clone producing the highest level of specific anti-dinitrophenyl antibody were expanded.

A hybridoma cell clone producing a high level of anti-dinitrophenyl antibody was incubated overnight in medium containing $^{14}$-C-leucine. The immunoglobulins in the supernatant were immunoprecipitated with rabbit anti-Fc and anti-light chain antisera and the precipitate analyzed sequentially by sodium dodecylsulfate-polyacrylamide gel electrophoresis and by isoelectric focusing.

In a second experiment a human spleen was isolated and treated as previously described. After cutting into pieces and forming a single cell suspension, red cells are removed employing a Ficoll-Hypaque gradient centrifugation. The viable cells are seeded at $2 \times 10^6$ cells/ml in tissue culture flasks in RPMI-1640 + 15% FCS + $10^{-5}$M 2-mercaptoethanol to which was added sheep red blood cells to a final concentration of one percent. After 4 days, the non-adherent cells were isolated and dead cells removed employing a Ficoll-Hypaque gradient centrifugaion. The buffy-coat was isolated and used for fusion under the same conditions as described previously. After incubation in HAT medium as described above clones were screened for IgG using $^{125}$I-labeled Staph. protein A. The production of IgG was not detected. The clones were then screened for IgM production using a test analogous to the Jerne Plaque Forming Assay. The test employs superimposed layers of agar, with SRBC and complement in one layer and the hybridoma cells in the other layer. Production of IgM results in lysis of the SRBC with formation of a plaque. Production of IgM was observed by plaque formation with at least one clone.

In accordance with the subject invention, a novel myeloma strain is provided which can be used for fusion with lymphoid cells to produce hybridomas. The hybridomas which are produced can be stably cultured in vitro and provide for a continuous source of monospecific monoclonal antibodies. In this manner, a wide variety of antibody compositions can be produced which are free of xenogeneic proteins. The complete human monoclonal antibodies can find wide uses, since they will be accepted by humans and are a homogenous composition having a unique binding site.

Although the foregoing invention has been described in some detail by way of illustration and example for purposes of clarity of understanding, it will be obvious that certain changes and modifications may be practiced within the scope of the appended claims.

What is claimed is:

1. A method for producing human-human hybridomas producing specific human monoclonal antibodies against a defined antigen site which comprises:
   fusing non-neoplastic lymphoid cells immunized against a defined antigen site with rapidly growing HAT sensitive human myeloma cells in a fusing medium at an approximately equivalent cell ratio to produce a cell mixture, wherein said myeloma cells are derived from U-266 myeloma cells;

dividing into each of a plurality of wells a sufficient number of cells of said cell mixture to encourage growth and incubating said cells in a nutrient medium for a sufficient time to expand the number of viable cells in each well;

growing the cells in HAT medium to produce clones free of HAT sensitive cells; and selecting for clones producing monoclonal antibodies for said defined antigen site.

2. A method according to claim 1, wherein said HAT sensitive myeloma cells are grown in the presence of 8-azaguanine before fusing.

3. A method according to claims 1 or 2, wherein said myeloma cell is U-266-AR1 having ATCC designation number CRL-8033 or a cell derived therefrom.

4. A method according to claim 2, wherein said lumphoid cells are derived from spleen.

5. A method according to claim 1, wherein said HAT medium contains at least about 30 i.u./ml of insulin.

* * * * *